(12) United States Patent
De Crecy

(10) Patent No.: US 7,939,315 B2
(45) Date of Patent: *May 10, 2011

(54) CONTINUOUS CULTURE APPARATUS WITH MOBILE VESSEL, ALLOWING SELECTION OF FILTER CELL VARIANTS

(76) Inventor: Eudes Francois Marie De Crecy, Gainesville, FL (US)

( * ) Notice: Subject to any disclaimer, the term of this patent is extended or adjusted under 35 U.S.C. 154(b) by 992 days.

This patent is subject to a terminal disclaimer.

(21) Appl. No.: 10/590,348

(22) PCT Filed: Feb. 23, 2005

(86) PCT No.: PCT/US2005/005616
§ 371 (c)(1),
(2), (4) Date: Jun. 8, 2007

(87) PCT Pub. No.: WO2005/083052
PCT Pub. Date: Sep. 9, 2005

(65) Prior Publication Data
US 2008/0220501 A1    Sep. 11, 2008

Related U.S. Application Data

(60) Provisional application No. 60/547,379, filed on Feb. 23, 2004.

(51) Int. Cl.
C12M 1/00 (2006.01)
C12M 3/00 (2006.01)

(52) U.S. Cl. ............... 435/293.1; 435/292.1; 435/294.1; 435/303.1

(58) Field of Classification Search ............... 435/289.1, 435/293.1, 298.2, 303.1–303.3, 304.3, 286.5, 435/292.1–294.1
See application file for complete search history.

(56) References Cited

U.S. PATENT DOCUMENTS

| | | | | |
|---|---|---|---|---|
| 4,686,189 A | * | 8/1987 | Redikultsev et al. | 435/286.5 |
| 4,703,010 A | * | 10/1987 | Yunker et al. | 435/173.8 |
| 5,017,490 A | * | 5/1991 | Taiariol et al. | 435/401 |
| 5,071,760 A | * | 12/1991 | Watanabe et al. | 435/394 |
| 5,256,298 A | | 10/1993 | Powell | |
| 5,525,305 A | | 6/1996 | Minekus et al. | |
| 6,066,497 A | | 5/2000 | Powell | |
| 6,537,772 B1 | * | 3/2003 | Alarcon et al. | 435/34 |
| 6,686,194 B1 | | 2/2004 | Mutzel et al. | |
| 2004/0029265 A1 | * | 2/2004 | Doi et al. | 435/297.1 |

FOREIGN PATENT DOCUMENTS

| | | | |
|---|---|---|---|
| CH | 552063 | * | 7/1974 |
| EP | 1 382 670 | | 1/2004 |
| JP | 3-30665 | | 2/1991 |
| WO | 89/07880 | | 9/1989 |
| WO | WO 94/09895 | | 5/1994 |

* cited by examiner

Primary Examiner — Walter D Griffin
Assistant Examiner — Shanta G Doe
(74) Attorney, Agent, or Firm — Young & Thompson

(57) ABSTRACT

Method and device that increases the rate of reproduction (through increased speed of reproduction and/or increased reproductive yield) of living cells in suspension or of any culturable organisms through the process of natural selection, said device comprising: a) a flexible, sterile tube (7) containing culture medium, b) a system of movable gates (clamps) (3, 4, 5) that divide the tube (97) into separate regions containing spent culture (downstream region), growing culture (growth chamber), and fresh growth medium (upstream region), c) a means of moving the gates and the tubing (13) such that a portion of the growth chamber and the associated culture can be clamped off and separated from the growth chamber, and such that a portion of fresh tubing containing unused medium can be joined with a portion of the culture and associated medium already present in the growth chamber.

63 Claims, 4 Drawing Sheets

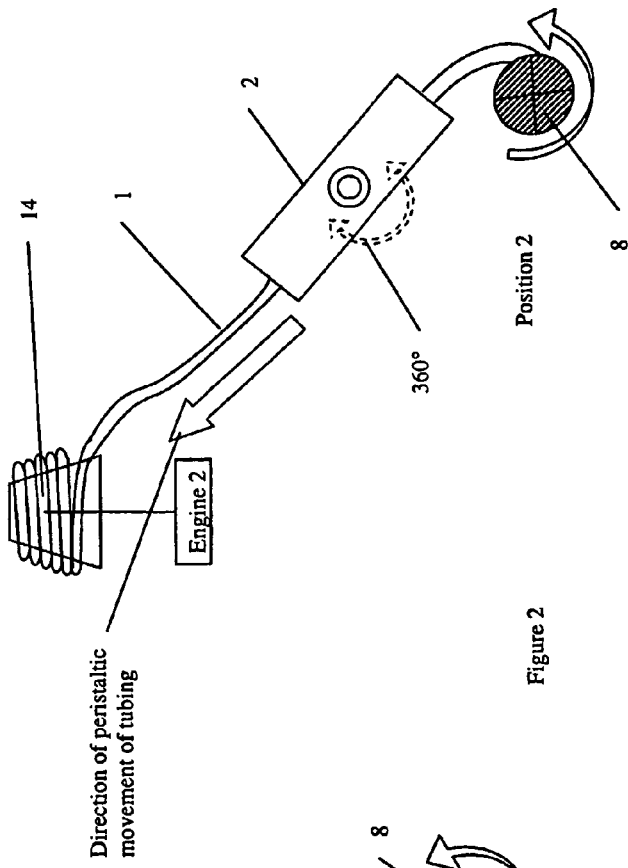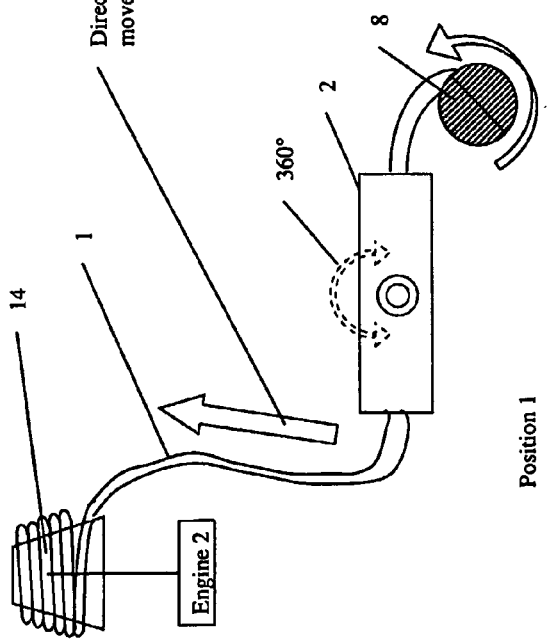
Figure 2
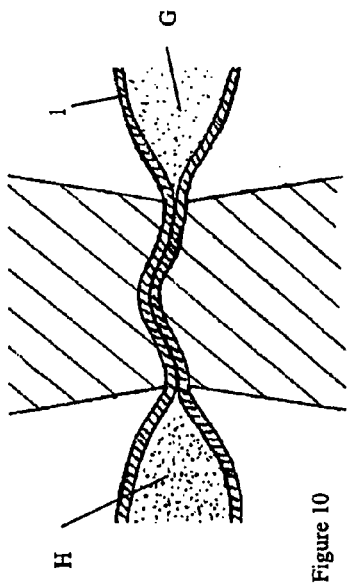
Figure 10

Fig. 3 - Tube full of medium before injection - Status T0. Fresh medium in every region of tubing A, B, C, D & E.

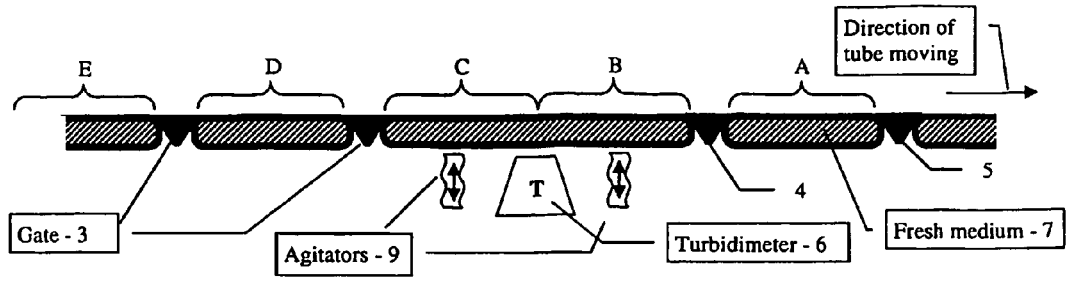

Fig. 4 - Chamber just after injection - Status T1, just at the beginning of first cycle. Culture growing in regions C & B.

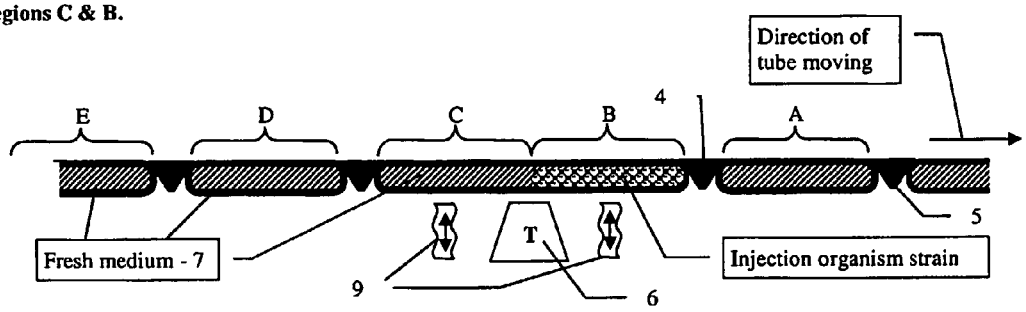

Fig. 5 - Status T2, during first growth cycle. Culture growing in regions C & B.

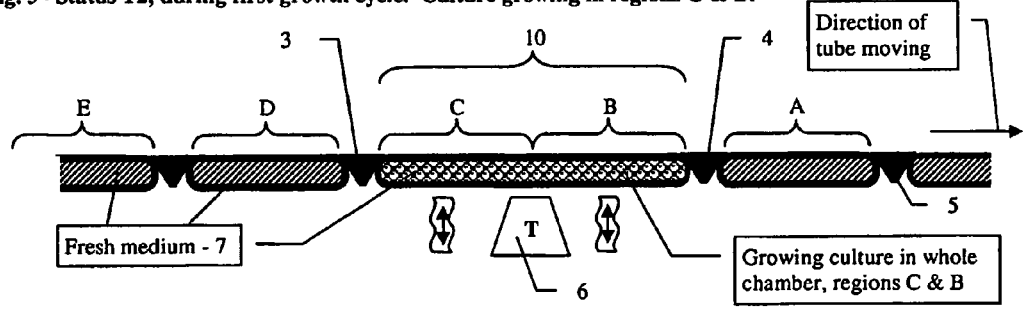

Fig. 6 - Status T3, just at the beginning of second growth cycle, just after first tube movement. Culture growing in region D & C.

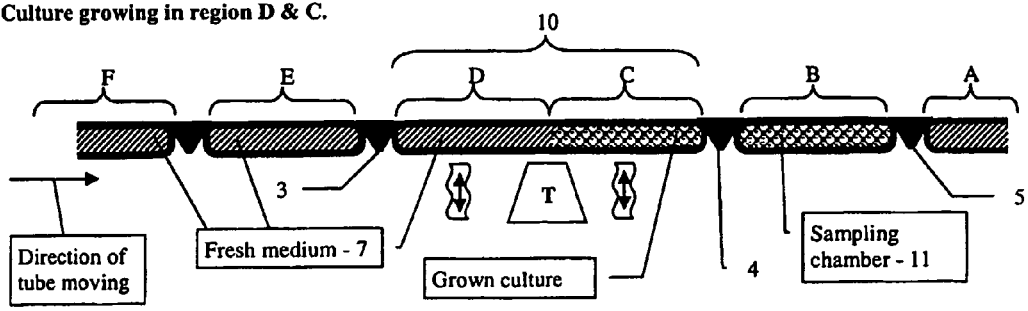

Fig. 7 - Status T4, during second growth cycle. Culture growing in regions D &C.
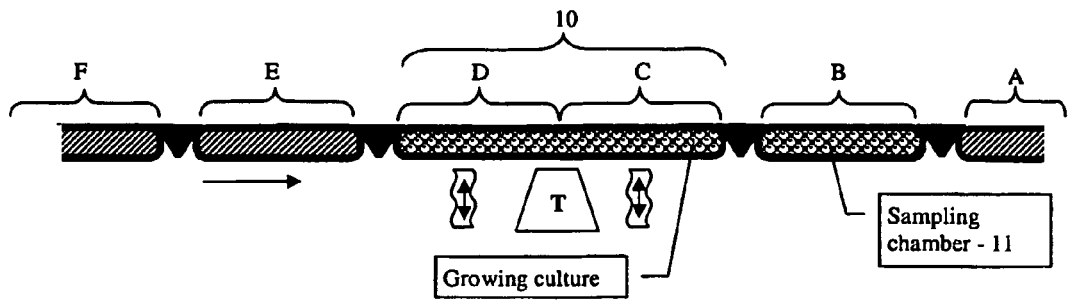
Fig. 8 - Status T5, just at the beginning of third growth cycle, just after second tube movement. Culture growing in regions E & D.
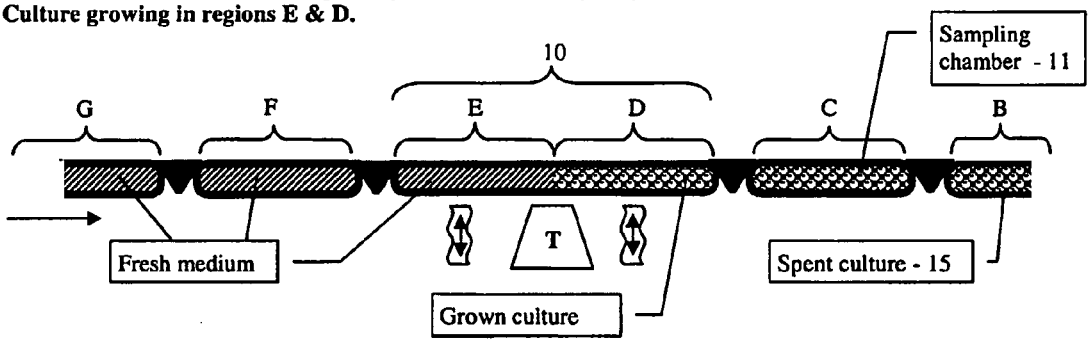
Fig. 9 - Status T6, during third growth cycle. Culture growing in regions E & D.
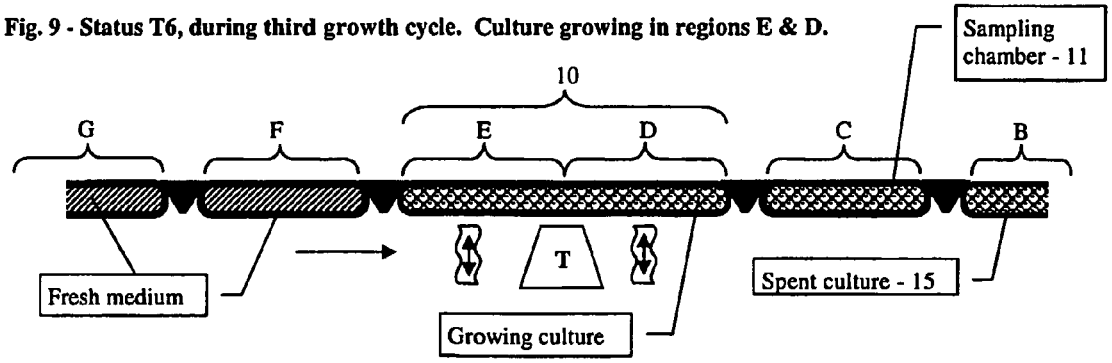

CONTINUOUS CULTURE APPARATUS WITH MOBILE VESSEL, ALLOWING SELECTION OF FILTER CELL VARIANTS

FIELD OF INVENTION

The described invention provides a method and a device that allow selection of living cells, with increased rates of reproduction and specific metabolic properties, in a liquid or semi-solid medium. For the process of selection (adaptive evolution), genetically variant organisms (mutants) arise in a population and compete with other variants of the same origin. Those with the fastest rate of reproduction increase in relative proportion over time, leading to a population (and individual organisms) with increased reproductive rate. This process can improve the performance of organisms used in industrial processes or academic purpose.

BACKGROUND OF INVENTION

Selection for increased reproductive rate (fitness) requires sustained growth, which is achieved through regular dilution of a growing culture. In the prior art this has been accomplished two ways: serial dilution and continuous culture, which differ primarily in the degree of dilution.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski & Travisano: *Dynamics of adaptation and diversification: a 10,000-generation experiment with bacterial populations.* 1994. Proc Natl Acad Sci USA. 15:6808-14), in experiments which clearly demonstrated consistent improvement in reproductive rate over period of years. This process is usually done manually, with considerable labor investment, and is subject to contamination through exposure to the outside environment. Serial culture is also Inefficient, as described in the following paragraph.

The rate of selection, or the rate of Improvement in reproductive rate, is dependent on population size (Fisher: *The Genetical Theory of Natural Selection.* 1930. Oxford University Press, London, UK). Furthermore, in a situation like serial transfer where population size fluctuates rapidly, selection is proportional to the harmonic mean ($\tilde{N}$) of the population (Wright: *Size of population and breeding structure in relation to evolution.* 1938. Science 87: 430-431), and hence can be approximated by the lowest population during the cycle.

Population size can be sustained, and selection therefore made more efficient, through continuous culture. Continuous culture, as distinguished from serial dilution, involves smaller relative volume such that a small portion of a growing culture is regularly replaced by an equal volume of fresh growth medium. This process maximizes the effective population size by increasing its minimum size during cyclical dilution. Devices allowing continuous culture are termed "chemostats" if dilutions occur at specified time intervals, and "turbidostats" if dilution occur automatically when the culture grows to a specific density.

For the sake of simplicity, both types of devices will hereafter be grouped under the term "chemostat". Chemostats were invented simultaneously by two groups in the 1950's (Novick & Szilard: *Description of the chemostat.* 1950. Science 112: 715-716) and (Monod: *La technique de la culture continue—Théorie et applications.* 1950. Ann. Inst. Pasteur 79:390-410). Chemostats have been used to demonstrate short periods of rapid improvement in reproductive rate (Dykhuizen D E. *Chemostats used for studying natural selection and adaptive evolution.* 1993. Methods Enzymol. 224: 613-31).

Traditional chemostats are unable to sustain long periods of selection for increased reproduction rate, due to the unintended selection of dilution-resistant (static) variants. These variants are able to resist dilution by adhering to the surface of the chemostat, and by doing so, outcompete less sticky individuals including those that have higher reproductive rates, thus obviating the intended purpose of the device (Chao & Ramsdell: *The effects of wall populations on coexistence of bacteria in the liquid phase of chemostat cultures.* 1985. J. Gen. Microbiol. 131: 1229-36).

One method and chemostatic device (the Genetic Engine) has been invented to avoid dilution resistance in continuous culture (patent U.S. Pat. No. 6,686,194-B1 filed by PASTEUR INSTITUT [FR] & MUTZEL RUPERT [DE]). This method uses valve controlled fluid transfer to periodically move the growing culture between two chemostats, allowing each to be sterilized and rinsed between periods of active culture growth. The regular sterilization cycles prevent selection of dilution-resistant variants by destroying them. This method and device achieves the goal, but requires independent complex manipulations of several fluids within a sterile (sealed) environment, including one (NaOH) which is both very caustic and potentially very reactive, quickly damaging valves, and posing containment and waste-disposal problems.

SUMMARY OF INVENTION

It is therefore an object of the present invention to provide an improved (and completely independent) method and device for continuous culture of organisms (including bacteria, archaea, eukaryotes and viruses) without interference from dilution-resistant variants. Like other chemostats, the device provides a means for regular dilution of a grown culture with fresh growth medium, a means for gas exchange between the culture and the outside environment, sterility, and automatic operation as either a chemostat or a turbidostat.

The present invention is designed to achieve this goal without any fluid transfer, including sterilization or rinsing functions. This represents a specific advantage of the present invention with respect to prior art in so far as it avoids the hazards and difficulties associated with sterilization and rinsing, including containment and complex fluid transfers Involving caustic solvents.

Continuous culture is achieved inside a flexible sterile tube filled with growth medium. The medium and the chamber surface are static with respect to each other, and both are regularly and simultaneously replaced by peristaltic movement of the tubing through "gates", or points at which the tube is sterilely subdivided by clamps that prevent the cultured organisms from moving between regions of the tube. UV gates can also (optionally) be added upstream and downstream of the culture vessel for additional security.

The present method and device are also an improvement over prior art insofar as they continually, rather than periodically, select against adherence of dilution-resistant variants to the chemostat surfaces, as replacement of the affected surfaces occurs in tandem with the process of dilution.

The tube is subdivided in a transient way such that there are regions that contain saturated (fully grown) culture, regions that contain fresh medium, and a region between these two, termed the growth chamber, in which grown culture is mixed with fresh medium to achieve dilution. The gates are periodically released from one point on the tube and replaced at another point, such that grown culture along with its associated growth chamber surface and attached static organisms, is removed by isolation from the growth chamber and replaced by both fresh medium and fresh chamber surface. By this method, static variants are specifically counter-selected by removal from the region in which selection is occurring (the growth chamber).

BRIEF DESCRIPTION OF DRAWINGS

Without being exhaustive and limiting, one possible general configuration will include several components as described hereafter. In the following the present invention is exemplarily explained on the basis of a preferred embodiment, thereby referring to the drawings in which:

FIG. 2 displays two possible positions of the device, exemplifying the fact that said thermostatically controlled box (2) and other pieces of said device associated with said culture chamber can be tilted to various degrees for agitation purposes, gas circulation and removal purposes, and purposes of guaranteeing the removal of granulated (aggregated) cells that might escape dilution by settling to the bottom.

FIGS. 3 to 9 represents said flexible tubing (1) in place in said thermostatically controlled box (2) and introduced through gates (3), (4) and (5) through which said tubing will stay during all steps of process and through which said tubing will move according to its peristaltic movement.

FIG. 3 symbolizes status T0 of the device in which all regions of said flexible tubing are filled with fresh medium before injection of the organism intended for continuous culture.

FIG. 4 symbolizes status T1 of said flexible tubing just after injection of organism strain.

FIG. 5 symbolizes status T2 of the device which is a growing period during which the culture grows in the region defined as the growth chamber (10) limited by said gates (3) and (4).

FIG. 6 symbolizes status T3 of device, just after the first peristaltic movement of tubing and associated medium, which determines the beginning of the second growing cycle, introducing fresh tubing and medium through movement of gate 3 simultaneous with a transfer of equivalent volume of tubing, medium, and grown culture out of the growth chamber region (10) and into the sampling chamber region (11) by movement of gate 4. It is critical to recognize that the tubing, the medium that is within the tubing, and any culture that has grown in that medium, all move together. Fluid transfer only occurs Insofar as fresh medium and grown culture mix together through agitation within the growth chamber region.

FIG. 7 symbolizes status T4 of the device which is the second growing cycle; during this cycle organisms that remain in the growth chamber after peristaltic movement of the tubing can now grow using nutrients provided in the fresh medium that is mixed with the remaining culture during this step.

FIG. 8 symbolizes status T5 of device, just after the second peristaltic movement of the tubing and the contained medium, which determines the beginning of the third growing cycle, introducing fresh tubing and medium through movement of gate 3 simultaneous with a transfer of equivalent volume of tubing, medium, and grown culture out of the growth chamber region (10) and into the sampling chamber region (11) by movement of gate 4.

FIG. 9 symbolizes status T6 of device which is the third growing cycle; this step is equivalent to status T4 and indicates the repetitive nature of further operations. Samples of selected organisms may be removed at any time from the sampling chamber region (11) using a syringe or other retrieval device.

FIG. 10 displays a possible profile of teeth determining a gate in the configuration which consists of two stacking teeth pinching flexible tubing. Gates could also be determined by single teeth pressing against a moveable belt, removable clamps, or other mechanisms that prevent movement of organisms through the gate and which can be alternately placed and removed in variable positions along the tubing.

DETAILED DESCRIPTION OF INVENTION

Figure 1:
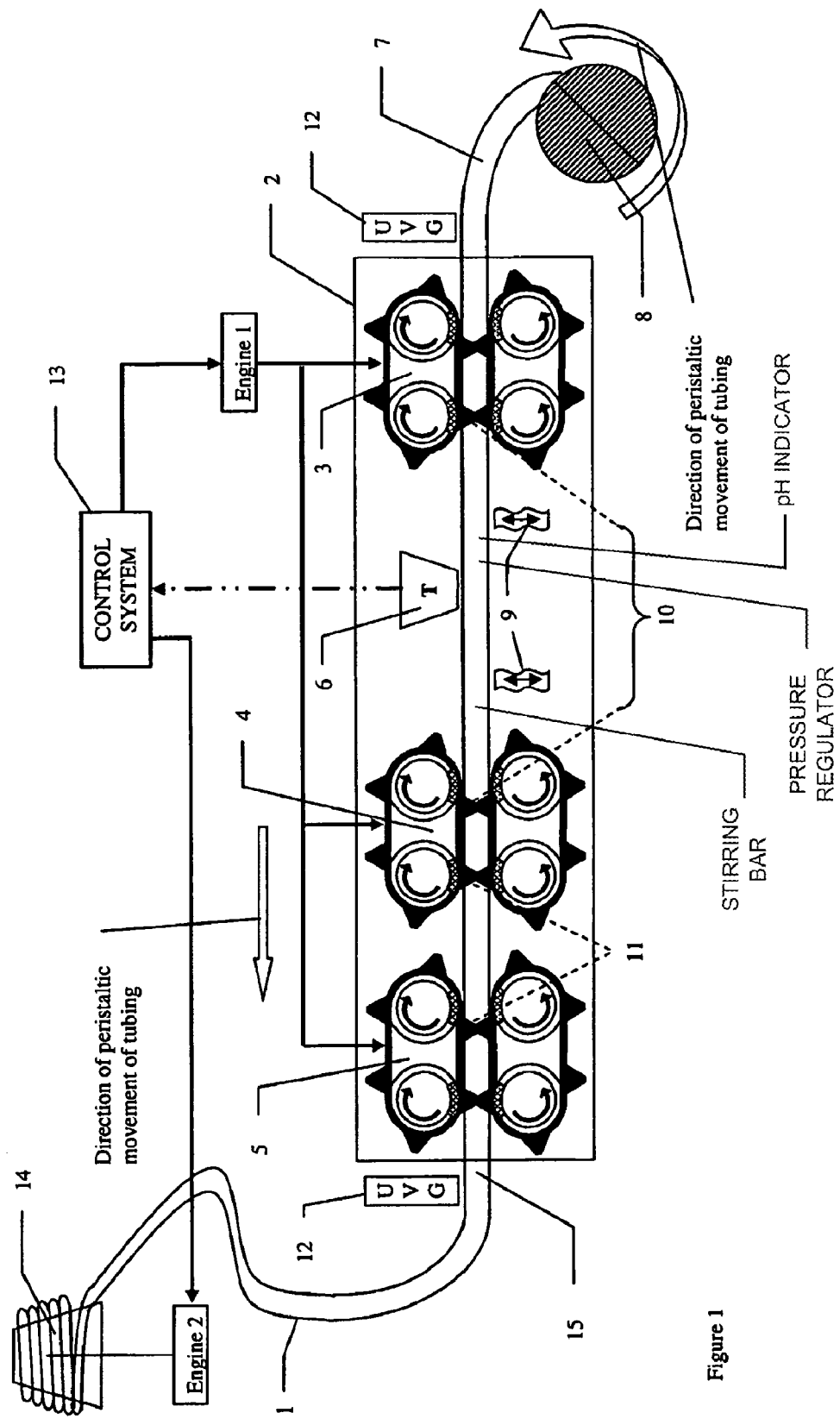
FIG. 1 displays an overall view of a possible configuration of the device in which:
(1) represents the flexible tubing containing the different regions of the device which are: upstream fresh medium (7), growth chamber (10), sampling chamber (11) and disposed grown culture region (15)
(2) represents the thermostatically controlled box allowing regulation of temperature according to conditions determined by user, and in which may be located:
  a. said growth chamber (10),
  b. said sampling chamber (11),
  c. upstream gate (3) defining the beginning of said growth chamber (10),
  d. downstream gate (4) defining the end of said growth chamber (10) and the beginning of said sampling chamber (11)
  e. second downstream gate (5) defining the end of said sampling chamber (11),
  f. turbidimeter (6) allowing the user or automated control system to monitor optical density of growing culture and to operate a feedback control system (13), allowing controlled movement of the tubing (1) on the basis of culture density (turbidostat function),
  g. one or several agitators (9).
It should be noted that the device elements listed in a-g may also be located outside of, or in the absence of, a thermostatically controlled box.
(7) represents the fresh medium in unused flexible tubing,
(8) represents a barrel loaded with fresh medium filled tubing, in order to dispense said fresh medium and tubing during operations.
(12) represents optional ultra-violet radiation gates,
(13) represents the control system that can consist of a computer connected with means of communication to different monitoring or operating interfaces, like optical density turbidimeters, temperature measurement and regulation devices, agitators and tilting motors, etc, that allow automation and control of operations,
(14) represents the optional disposal barrel on which to wind up tubing containing disposed grown culture filled tubing,
(15) represents disposed grown culture located downstream of said sampling chamber.

The basic operation of the device is depicted in FIGS. 3 through 9. One potential configuration for the present device is shown in FIG. 1, as it appears after having been loaded with a fresh tube of sterile medium (shown divided into regions A-H by said gates (3), (4) and (5)).

Inoculation of the device with the chosen organism could be achieved by introduction of the organism into the growth chamber (FIG. 3), through injection (FIG. 4, region B). The culture would then be allowed to grow to the desired density and continuous culture would begin (FIG. 5).

Continuous culture would proceed by repetitive movements of the gated regions of tubing, which may be translucent or transparent. This involves simultaneous movements of the gates, the tubing, the medium, and any culture within the tubing. The tubing will always move in the same direction; unused tubing containing fresh medium (and hereafter said to be 'upstream' of the growth chamber (7)) will move into the growth chamber and mix with the culture remaining there, providing the substrate for further growth of the organisms contained therein. Before Introduction into the growth chamber region, this medium and its associated tubing will be maintained in a sterile condition by separation from the growth chamber by the upstream gates (3). Used tubing containing grown culture will simultaneously be moved 'downstream' and separated from the growth chamber by the downstream gates (4).

Gate configuration is not a specific point of the present patent application. For example, in a given configuration, gates can be designed through one chain of multiple teeth simultaneously moved or in another configuration separated in distinct synchronized chains as depicted in FIG. 1. Gates can consist of a system made of two teeth pinching the tubing in a stacking manner as described in FIG. 10, avoiding contamination between regions G and H of the tubing through the precision of the interface between the teeth. In another configuration, sterile gates can be obtained by pressing one tooth against one side of the tubing and thereby pressing the tubing tightly against a fixed chassis along which tubing is slid during its peristaltic movement, as sketched in FIG. 3 to 9, marks 3, 4 and 5.

Said thermostatically controlled box (2) is obtained by already known means such as a thermometer coupled with a heating and cooling device.

Aeration (gas exchange), when required for growth of the cultured organism or by the design of the experiment, is achieved directly and without mechanical assistance by the use of gas permeable tubing. For example and without being limiting, flexible gas permeable tubing can be made of silicone. Aeration could be achieved through exchange with the ambient atmosphere or through exchange with an artificially defined atmosphere (liquid or gas) that contacts the growth chamber or the entire chemostat. When an experiment demands anaeroblosis the flexible tubing can be gas impermeable. For example and without being limiting, flexible gas impermeable tubing can be made of coated or treated silicone.

For anaerobic evolution conditions, regions of the tubing can also be confined in a specific and controlled atmospheric area to control gas exchange dynamics. This can be achieved either by making said thermostatically controlled box gastight and then injecting neutral gas into it or by placing the complete device in an atmosphere controlled room.

Counter-selection of static variants is achieved by replacement of the growth chamber surface along with growth medium.

The device is further designed to be operable in a variety of orientations with respect to gravity, that is, to be tilted as shown by FIG. 2, along a range of up to 360°.

Dilution-resistant variants may avoid dilution by sticking to one another, rather than to the chamber wall if aggregated cells can fall upstream and thereby avoid removal from the chamber. Hence it is desirable that the tubing generally be tilted downward, such that aggregated cells will fall toward the region that will be removed from the growth chamber during a cycle of tube movement. This configuration involves tilting the device so that the downstream gates are below the upstream gates with respect to gravity.

The growing chamber can be depressurized or over pressurized according to conditions chosen by the experimenter. Different ways of adjusting pressure can be used, For instance applying vacuum or pressurized air to the fresh medium and tubing through its upstream extremity and across the growth chamber; another way of depressurizing or overpressurizing tubing can be done by alternate pinching and locking tubing upstream of the growth chamber.

When the medium is contained in gas permeable tubing, air bubbles may form within the medium. These will rise to the top of a sealed region of tubing and become trapped there until the movement of the region (and the gates defining it) releases the region into either the growth chamber, the sampling chamber or the endpoint of the chemostat (FIG. 6, regions D-C, B or A, respectively). If the device is tilted downward such bubbles will accumulate in the growth chamber or sampling chamber and displace the culture. The device is designed to periodically tilt upward for a cycle of the tube movement, allowing for the removal of accumulated gas from said chambers.

Tilting movements of the device, and/or shaking of the growth chamber by an external device (9) can be used to decrease aggregation of cells within the growth chamber. Alternatively, one or several stirring bars can be included in the tubing filled with fresh medium before sterilization and magnetically agitated during culture operations.

The proportional length of the regions of fresh medium defined by the upstream gates as compared to the length of the culture chamber will define the degree of dilution achieved during a cycle.

The frequency of dilution can be determined either by timing (chemostat function) or by feedback regulation whereby the density of the culture in the growth chamber is measured by a turbidimeter (FIG. 1—mark 6) and the dilution cycle occurs when the turbidity reaches a threshold value (turbidostat function).

The sampling chamber allows withdrawing grown culture in order to analyze the outcome of an experiment, collect organisms with improved growth rate for further culture, storage, or functional implementation, or other purposes such as counting the population, checking the chemical composition of the medium, or testing the pH of grown culture. In order to achieve permanent monitoring of pH inside growth chamber, tubing can include by construction a pH indicator line embedded/encrusted in the wall of the tubing.

Any form of liquid or semi-solid material can be used as a growth medium in the present device. The ability to utilize semi-solid growth substrates is a notable advancement over prior art. The growth medium, which will define the metabolic processes improved by the selection process, can be chosen and defined by the user.

If needed, this device can contain multiple growth chambers, such that the downstream gates of one growth chamber become the upstream gates of another. This could, for example, allow one organism to grow alone in the first chamber, and then act as the source of nutrition for a second organism (or virus) in the second chamber.

This device and method allows researchers and product developers to evolve any strain of culturable living cells in suspension through sustained growth (continuous culture); the resulting improved organism can constitute a new strain or species. These new organisms can be identified by mutations acquired during the course of culture, and these mutations may allow the new organisms to be distinguished from their ancestors genotype characteristics. This device and method allow the researcher to select new strains of any living organism by segregating individuals with improved rates of reproduction through the process of natural selection.

What is claimed is:

1. A device that increases the rate of reproduction through increased speed of reproduction and/or increased reproductive yield of living cells in suspension or of any culturable organisms through the process of natural selection, said device comprising:
   a) a flexible, sterile tube containing culture medium;
   b) a system of clamps, each capable of open and closed positions, the clamps being positioned so as to be able to divide the tube into a downstream region containing spent culture, a growth chamber containing growing culture, and an upstream region containing fresh growth medium;
   c) a means of moving the clamps and the tubing; and
   d) a control system that measures culture density in the growth chamber, and controls the means of moving the clamps and the tubing based on the measured culture density.

2. The device according to claim 1, wherein the tubing is gas permeable.

3. The device according to claim 1, wherein the tubing is gas impermeable.

4. The device according to claim 1, wherein the tubing is transparent or translucent, to allow the measurement of turbidity.

5. The device according to claim 1, wherein the device is constructed and arranged to selectively subject the growth chamber tubing and associated media and culture to a pressure that is either higher or lower than ambient atmosphere.

6. The device according to claim 1, wherein the tubing allows the measure of pH of medium by inclusion of a pH indicator in the tubing composition or lining.

7. The device according to claim 1, wherein the device is constructed and arranged to selectively raise or lower a temperature of the growth chamber tubing and associated media and culture.

8. The device according to claim 1, wherein device is constructed and arranged to agitate the growth chamber tubing and associated media and culture.

9. The device according to claim 8, wherein the tubing includes at least one stirring bars.

10. The device according to claim 1, wherein the device is structured and arranged to subject a confined region of the tubing to a specific and controlled atmosphere to control gas exchange dynamics.

11. The device according to claim 1, wherein the device is structured and arranged to tilt the growth chamber tubing and associated media and culture.

12. A method that increases the rate of reproduction through increased speed of reproduction and/or increased reproductive yield of living cells in suspension or of any culturable organisms through the process of natural selection, comprising:
   a) providing a sterile tube containing sterile growth medium and divided by a plurality of gates into a fresh medium chamber and a growth chamber, and inserting an initial culture in the growth chamber as a starter culture;
   b) maintaining growth conditions according to experimental requisites;
   c) after a certain growth of the culture density, adjusting position of the gates so as to move portions of the sterile growth medium and of grown culture, respectively, into and out of the growth chamber, allowing a portion of grown culture remaining in the growth chamber to mix with the introduced portion of the sterile growth medium and continue to grow;
   d) reproducing steps b) and c) to achieve continuous culture and selection of variants with increased reproductive rates; and
   e) withdrawing on demand a sample of grown culture.

13. A method according to claim 12 wherein applying a simultaneous peristaltic movement of the gates, the tubing, and the medium and the culture within the tubing, allows provision of a certain quantity of the sterile growth medium to a first end of the growth chamber while an equal quantity of culture is isolated and removed through an opposite end of said growth chamber, terminating a growth cycle and starting a new growth cycle.

14. A method according to claim 12 wherein steps b) and c are repeated without contamination of isolated growing chamber and without proliferation of a dilution-resistant population.

15. A method according to claim 12, further comprising maintaining growth conditions, said growth conditions including at least one of temperature, pressure, optical density, chemical acidity, agitation and aeration with various gases.

16. A method according to claim 12, further comprising tilting the device and operating agitators to mix the growing culture.

17. A device that increases the rate of reproduction through increased speed of reproduction and/or increased reproductive yield of living cells in suspension or of any culturable organisms through the process of natural selection, said device comprising:
   a continuous length of flexible, sterile tubing;
   a system of clamps positioned at points along a section of the tubing, each of the clamps being positioned and arranged so as to be able to controllably pinch the tubing by putting said clamp into a closed position in which the tubing is divided into separate regions on respective sides of said clamp, the separate regions on respective sides of said clamp being merged back into a single region when said clamp is returned to an open position;
   wherein the clamps and tubing are arranged so that the tubing is clamped at first through fourth points along the tubing, defining a fresh medium chamber, a growth chamber, and a sampling chamber downstream of the first through third points, respectively; and
   wherein a volume of the growth chamber delimited by said points two and three is greater than a volume of the fresh medium chamber and the sampling chamber;
   wherein the system of clamps is constructed so that, in a repeating pattern, the tubing is clamped upstream of the first point, the tubing is clamped at a point between the second and third points, and the second point is returned to the open position, thereby subdividing the growth chamber into an upstream portion and a downstream portion, merging the fresh medium chamber and the upstream portion, and thereby defining new first through fourth points and said fresh medium chamber, said growth chamber, and said sampling chamber.

18. The device according to claim 17, wherein the tubing is gas permeable.

19. The device according to claim 17, wherein the tubing is gas impermeable.

20. The device according to claim 17, wherein the tubing is translucent.

21. The device according to claim 17, wherein the tubing is transparent.

22. The device according to claim 17, wherein contents of the tubing in the second region can be controllably depressurized or over pressurized relative to ambient atmosphere.

23. The device according to claim 17, further comprising a pH indicator in the tubing.

24. The device according to claim 17, further comprising a heating and cooling device that can control a temperature of contents of the tubing.

25. The device according to claim 17, further comprising an agitator.

26. The device according to claim 25, wherein the agitator comprises at least one stirring bar.

27. The device according to claim 17, wherein regions of the tubing can be confined in a specific and controlled atmospheric area to control gas exchange dynamics.

28. The device according to claim 17, further comprising a device to control tilting of the growth chamber.

29. A method that increases the rate of reproduction through increased speed of reproduction and/or increased reproductive yield of living cells in suspension or of any culturable organisms through the process of natural selection, said method comprising steps of:
    providing a continuous length of flexible, sterile tubing;
    providing a system of clamps positioned at points along a section of the tubing, each of the clamps being positioned and arranged so as to be able to controllably pinch the tubing by putting said clamp into a closed position in which the tubing is divided into separate regions on respective sides of said clamp, the separate regions on respective sides of said clamp being merged back into a single region when said clamp is returned to an open position;
    placing culture medium in the tubing;
    closing the clamps at first through fourth points along the tubing to define first through third regions downstream of the first through third points, respectively, wherein the volume of the second region delimited by said points two and three is greater than a volume of the first and third regions;
    introducing said culturable organism into the second region between the second and third points, and allowing the culture to grow in the culture medium; and
    repeating a step that comprises clamping the tubing upstream of the first point, clamping the tubing at a point between the second and third points, and returning the second point to the open position, thereby subdividing the second region into an upstream portion and a downstream portion, merging the first region and the upstream portion, and thereby defining new first through fourth points and first through third regions.

30. The method of claim 29, wherein applying a simultaneous peristaltic movement of the clamps, the tubing, and the medium and the culture within the tubing, allows provision of a certain quantity of fresh said medium to the second region of the tubing while an equal quantity of said culture is isolated and removed through an opposite end of said second region, terminating one growth cycle and starting a new growth cycle.

31. The method of claim 29, further comprising a step of controlling a pressure of contents of the tubing in the second region.

32. The method of claim 29, further comprising a step of controlling a temperature of contents of the tubing.

33. The method of claim 29, further comprising a step agitating contents of the tubing.

34. The method of claim 29, further comprising a step of providing a specific and controlled atmospheric area around the tubing to control gas exchange dynamics.

35. The method of claim 29, further comprising a step of controllably tilting of the second portion of the tubing.

36. A device for growing living cells in a continuous manner, comprising:
    flexible tubing containing culture medium; and
    a system of clamps, each capable of open and closed positions, the clamps being positioned so as to be able to divide the tubing into:
        i) an upstream region containing unused culture medium;
        ii) a downstream region containing spent culture medium; and
        iii) a growth chamber region for growing said cells disposed between the upstream and downstream regions; and
    a control system that controls operation of the clamps;
    wherein the system of clamps is constructed and arranged, under control of the control system, to open and close so as to clamp off and define the growth chamber region of the tubing between the upstream and downstream regions of the tubing, and to cyclically redefine the growth chamber region of the tubing so that a first portion of the previously defined growth chamber region becomes a portion of the downstream region of the tubing, and a portion of the previously defined upstream region of the tubing becomes a portion of the growth chamber region of the tubing; and
    wherein the control system measures culture density in the growth chamber, and controls the system of clamps based on the measured culture density.

37. The device according to claim 36, wherein the system of clamps is structured and arranged so that each of the clamps does not move with respect to the tubing when said clamp is in the closed position.

38. The device according to claim 36, wherein the tubing is gas permeable.

39. The device according to claim 36, wherein the tubing is gas impermeable.

40. The device according to claim 36, wherein the tubing is one of transparent and translucent to permit a turbidity meter to determine the density of the culture.

41. The device according to claim 36, wherein the device further comprises a pressure regulator constructed to change a pressure of the growth chamber portion of the tubing relative to ambient pressure.

42. The device according to claim 36, wherein the tubing comprises a pH indicator.

43. The device according to claim 36, further comprising a temperature regulator constructed to control the temperature of the growth chamber region of the tubing.

44. The device according to claim 36, wherein the device further comprises an agitator constructed to allow agitation of the growth chamber portion of the tubing.

45. The device according to claim 44, wherein the agitator comprises at least one stirring bar.

46. The device according to claim 36, wherein said growth chamber region comprises one or more growth chambers containing culture medium.

47. A method for growing cells in continuous manner, comprising:
    a) providing flexible tubing and a system of clamps, each of the clamps being capable of open and closed positions, the clamps being positioned so as to be able to divide the tubing into:
        i) an upstream region containing unused culture medium;

ii) a downstream region containing spent culture medium; and
iii) a growth chamber region for growing said cells disposed between the upstream and downstream regions; and
iv) a control system that controls operation of the clamps; and b) under control of the control system, closing selected ones of the clamps on the tubing to define the growth chamber region of the tubing between the upstream and downstream regions of the tubing, and introducing viable cells into the growth chamber region;

c) cyclically closing and opening selected ones of the clamps to redefine the growth chamber region of the tubing so that a first portion of the previously defined growth chamber region becomes a portion of the downstream region of the tubing, and a portion of the previously defined upstream region of the tubing becomes a portion of the growth chamber region of the tubing; and d) repeating step c) until a sufficient amount of cells has been grown;

wherein the control system measures culture density in the growth chamber, and controls the system of clamps based on the measured culture density.

48. The method according to claim 47, comprising the further step of withdrawing a sample of living cells from said culture medium from said downstream region.

49. The method according to claim 47, further comprising isolating said living cells from said downstream region.

50. The method according to claim 47, wherein the living cells are selected from the group consisting of Yeast, Bacteria, Archae, Eukaryotes, and Viruses.

51. The method according to claim 47, wherein said growth chamber region comprises one or more growth chambers containing culture medium.

52. The method according to claim 47, wherein one or more species of organism are grown in said growth chambers.

53. The method according to claim 47, wherein the sufficient amount of cells of step d) is defined as a pre-determined density level of the cells.

54. The method according to claim 47, wherein the tubing is gas permeable.

55. The method according to claim 47, wherein the tubing is gas impermeable.

56. The method according to claim 53, wherein the tubing is one of transparent and translucent, a turbidimeter being used to determine the density level of the cells.

57. The method according to claim 47, further comprising regulating the pressure of the growth chamber portion of the tubing relative to ambient pressure.

58. The method according to claim 47, further comprising measuring a pH of the culture medium in the growth chamber region.

59. The method according to claim 47, further comprising regulating the temperature of the growth chamber region with a temperature regulator constructed to control the temperature of the growth chamber region of the tubing.

60. The method according to claim 47, further comprising agitating the culture medium in the growth chamber region with an agitator.

61. The method according to claim 60, wherein the agitator comprises at least one stirring bar.

62. The device of claim 1, wherein each of the clamps does not move with respect to the tube when said clamp is in the closed position.

63. The device of claim 62, wherein the means of moving the clamps and the tubing operates in a manner such that a portion of the growth chamber and the associated culture can be clamped off and separated from the growth chamber, and such that a portion of fresh tubing containing unused medium can be joined with a portion of the culture and associated medium already present in the growth chamber.

* * * * *